United States Patent [19]
Allington

[11] Patent Number: 5,135,628
[45] Date of Patent: Aug. 4, 1992

[54] PULSED FIELD GEL ELECTROPHORESIS OF LARGE DNA

[75] Inventor: Robert W. Allington, Lincoln, Nebr.

[73] Assignee: Isco, Inc., Lincoln, Nebr.

[21] Appl. No.: 348,679

[22] Filed: May 5, 1989

[51] Int. Cl.$^5$ .................... G01N 27/26; B01D 57/02
[52] U.S. Cl. .................... 204/182.8; 204/299 R
[58] Field of Search .................... 264/299 R, 182.8

[56] References Cited

FOREIGN PATENT DOCUMENTS

| | | | |
|---|---|---|---|
| 359107 | 3/1990 | European Pat. Off. | 204/299 R |
| 2605472 | 4/1988 | France | 204/299 R |
| 8700635 | 1/1987 | PCT Int'l Appl. | 204/299 R |

OTHER PUBLICATIONS

Steven M. Clark et al. "Novel Instrument for Separating Large DNA Molecules with Pulsed Homogeneous Electric Fields" *Science*, 241: 1203–1205 (1988).

Chantal Turmel, "Molecular detrapping and band narrowing with high frequency modulation of pulsed field electrophoresis" Nucleic Acids Research, 18(3) [1990] 569–575.

Gilles Roy et al. "Inexpensive and simple set–up for field inversion gel electrophoresis" Nucleic Acids Research 16(3) [1988] 768.

C. D. Porter et al., "BBC microcomputer controlled field inversion gel electrophoresis" Computer applications in the biosciences:CABIOS, 4(2) [1988] 271–273.

*Primary Examiner*—John Niebling
*Assistant Examiner*—John S. Starsiak, Jr.
*Attorney, Agent, or Firm*—Vincent L. Carney

[57] ABSTRACT

An electrophoresis apparatus 10 has a power supply 12, an electrophoresis gel system including the tank 85 and an adjustable switching means 42 connected together for controlling the electric field force, electric field angle and the pulse duration to resolve DNA molecules greater than 1,000 kb in length along straight, unbent lanes within a gel. The electrophoresis system 10 permits adjustment of the pulse durations through a range from generally one-tenth of a second to shorter ranges. It permits the adjustability of the electric field force, electric field angle and the pulse duration so that it may have: (1) pulse durations in a range that maintains the pulse durations shorter than one-tenth of a second; (2) an angle or angles of two fields up to 180 degrees with respect to each other; (3) a side range of intensities of the fields; and (4) any number of repetitions of pulses of the fields before changing the angle of the two fields with respect to each other.

22 Claims, 4 Drawing Sheets

PULSED FIELD GEL ELECTROPHORESIS OF LARGE DNA

BACKGROUND OF THE INVENTION

This invention relates to pulsed field gel electrophoresis of large DNA.

In the process of separating DNA molecules by electrophoresis, an electric field is applied across a gel to separate DNA molecules as they are moved by the field through the gel.

It is known to use the characteristics of the field established across the gel to control the electrophoresis for maximum separation. The fractionation of different molecular weight DNAs is presumably due to the sieving effect of the agarose gel matrix rather than differing electrophoresis mobilities of the DNAs as found in a free (completely liquid) medium.

In one prior art technique of electrophoresis that has been used for separating DNA, a static, unidirectional electric field is applied to a DNA sample resulting in the migration of the DNA molecules through the agarose.

This technique has a disadvantage in that it can successfully be applied to DNAs up to a few hundred kilobase. One embodiment of this technique can be successfully applied to DNAs up to 100 kilobase pairs (kb, about 60 million daltons, and another embodiment using low agarose gel concentration was described by Fangman, W.L. (1978), "Separation of very large DNA molecules by gel electrophoresis," Nucleic Acids Res. 5 (3):653-665, separated DNA molecules up to 750 kb. However, due to the inordinately long running times that are required when using low agarose concentrations gels and the inherent fragility of these gels, the method of Fangman is impractical for routine lab use.

Several other techniques are known to be successful in resolving large chromosome fragments sized (larger than 1 megabase) DNA molecules in agarose gels. These techniques are different forms of pulsed field gel electrophoresis (PFGE) which is the resolution of large sized DNA molecules by periodically changing the electric field pattern during electrophoresis. The changes in field pattern reorient the DNA molecules and the separating medium, thus improving DNA separation. In the prior art PFGE techniques, the pulse lengths are of sufficiently long duration to change the gross configuration of the DNA, being larger than one second in duration for the separation of large DNA. The changes in gross configuration are affected by the pulse duration and changes in direction and may vary from realigning direction of a substantially straight elongated strand to creating hooks or staircase-shaped strands.

Hooking and forking configurationsal changes in DNA during electrophoresis is described by Smith, S.B., Aldridge, P.k., and Calles, J.B. (1989), "Observation of Individual DNA Molecules Undergoing Gel Electrophoresis," Science 243:203-206. In this paper, Smith reported that DNA undergoes gross conformational changes during continuous (non-pulsed) electrophoresis. Gross changes are shown in a time scale of one second.

Historically, pulsed field electrophoresis was reported as early as 1959 by Schwalbe, M.I. (1959), "Pulsed Field Electrophoresis," International Conf. on Medical Electronics, pp. 603-604, Paris, in the separation of human plasma proteins using paper strip electrophoreseis but there are many other prior art embodiments. The technique described in that paper has not been used successfully to separate large DNA molecules.

In 1984, a pulsed field gel electrophoresis system (Pulsed Field Gradient Gel Electrophoresis), was reported in Schwartz, D.C. and Cantor, C.R. (1984), "Separation of Yeast Chromosome-sized DNAs by Pulsed Field Gradient Gel Electrophoresis," Cell 37 67-75; (1984) and in U.S. Pat. No. 4,473,452. This method was used in the separation of chromosome sized DNA.

In this method, an array of electrodes in a square submarine gel tank was used and two electric fields, one non-uniform and one uniform were pulsed in cycles of seconds or longer in two transverse directions in the plane of the gel; resulting in the resolution of DNA molecules with sizes from 30 to 2,000 kb. Schwartz, D.C. and Cantor, C.R. (1984), "Separation of Yeast Chromosome-sized DNAs by Pulsed Field Gradient Gel Electrophoresis," Cell 37:67-75; (1984) on page 68, and especially in table 1, describes 8 second perpendicular pulses of a uniform field.

A variation of the above was described in McPeek, F.D., Jr., Coyle-Morris, J.F., Gemmill, R.M. (1986), "Separation of Large DNA Molecules by Modified Pulsed Field Gradient Gel Electrophoresis," Anal. Biochemistry 156:274-285. A combination of non-uniform fields pulsing in the X- and Y-directions was examined. The results of this study showed that a cyclic pattern of non-uniform fields resulted in better DNA resolution in the PFGE System. More importantly, these studies demonstrated the significance of the pulsed field duration in times of seconds or longer in the resolution of different sized large DNA molecules. This led these researchers to conclude that the electric field switching time is a sensitive variable in OFAGE and probably all pulsed field gel electrophoresis techniques.

The field gradient techniques described by Schwartz, D.C. and Cantor, C.R. (1984) and by McPeek, F.D., Jr., Coyle-Morris, J.F., Gemmill, R.M. (1986) have a disadvantage in that the resulting pattern is non-linear and forms bent lanes, which seems to be due to the electric field gradient across the agarose gel. This gradient causes the direction of migration of the DNA molecules to vary depending on their location in the gel. The resulting bent lanes are of considerable consequence since this makes any lane-to-lane comparisons for molecular weight estimation difficult.

To alleviate this bent lane problem, the agarose gel has been oriented vertically so the electric field gradient is transverse, (across the thickness of the gel). This transverse alternating field is pulsed with pulse durations of seconds or more for separating large DNA. This method of electrophoresis (TAFE) eliminates the bent lanes but presets the value of the pulsed electric field angle to 115 degrees at the top of the gel to 165 degrees at the bottom. These methods are described in Gardiner, K., Laas W. and Patterson, D. (1986), "Fractionation of Large Mammalian DNA Restriction Fragments Using Vertical Pulsed-Field Gradient Gel Electrophoresis," Somatic Cell Mol. Genet. 12:185-195, and in Gardiner, K. and Patterson, D. (1988), "Transverse Alternating Electrophoresis," Nature 331:371-372.

This method has a disadvantage in that the pulse duration is long and the electric field angle varies from 115 to 165 degrees along the gel although it is not adjustable. The field angle and pulse duration cause the DNA to move at an angle and the angle is a factor in PFGE which affects the separation resolution of DNA molecules. Thus, by causing the electric field angle to vary over a range of unadjustable values, the versatility of a technique related to a particular device is severely limited.

A simpler approach is described in Carle, G.F., Frank, M. and Olson, M.V. (1986), "Electrophoretic Separations of Large DNA Molecules by Periodic Inversion of the Electric Field," *Science* 232:65–68. In this approach, the electrophoretic separation of DNA molecules up to 700 kb is accomplished by using a method termed field inversion gel electrophoresis (FIGE). In FIGE, DNA molecules are subjected to a uniform electric field which is periodically inverted 180 degrees. Net forward migration of the DNA is achieved by differing the duration or the voltage of the forward and reversed fields.

FIGE has a disadvantage in that the resolution of DNA molecules larger than 200 kb is not as good as in the foregoing PFGE techniques. Although the problem of lane bending is eliminated, the rate of DNA migration is not monotonically related to size. Molecules of different sizes may have the same mobility. Thus, FIGE may not result in reliable DNA separation based on size.

The difficulty was explained by Sutherland et al. in Sutherland, J.C., Monteleone, D.C., Mugavero, J.H. and Trunk, J. (1987), "Unidirectional Pulsed-Field Electrophoresis of Single- and Double-stranded DNA in Agarose Gels: Analytical Expressions Relating Mobility and Molecular Length and Their Application in the Measurement of Strand Breaks," *Anal. Biochemistry* 162:511–520. This paper describes an attempt to solve this problem. They reexamined DNA agarose gel separation using unidirectional pulsed field electrophoresis where the electric field is pulsed in one direction without inversion. Although these authors show that DNA size is a function of mobility in their system, the upper DNA resolution limit is in the range of 400 kb.

In another prior art technique described by Chu and coworkers in Chu, G., Vollrath, D. and Davis, R.W. (1986), "Separation of Large DNA Molecules by Contour-clamped Homogeneous Electric Fields," *Science* 234:1582–1585, the electric field vector was examined and a conclusion was reached that the limitations of a non-uniform electric field could be overcome by applying a contoured-clamped homogeneous electric field (CHEF) which alternates between two orientations. He concluded that changing the electric field angle from 0 to 153 degrees improved separation of DNA up to 200 kb.

To apply a contoured-clamped homogeneous electric field (CHEF) which alternates between two orientations, the CHEF system uses a hexagonal tank with multiple electrodes, which effectively sets the value of the uniform electric field angle to 120 degrees and clamps each electrode to the appropriate potential. In the same article, Chu and his coworkers also report on a square tank using uniform and perpendicular fields.

Thus, with this system, Chu and coworkers demonstrated that the separation of large DNA molecules is a function of the electric field angle and electric field pulse duration. This apparatus has the disadvantage that the field angle cannot easily be varied. A way of varying field angle is descrived in Serwer in Serwer, P. (1987), "Gel Electrophoresis with Discontinuous Rotation of the Gel: An Alternative to Gel Electrophoresis with Changing Direction of the Electric Field," *Electrophoresis* 8:301–304. This paper describes the effect of changing the electric field angle by mechanically rotating the agarose gel, (Rotating gel electrophoresis, RGE).

CHEF and RGE have a disadvantage in that the pulse cycle times are longer than several seconds for separating large DNA, causing periodic and frequent changes in the gross configuration of the DNA, and possible reduction in the resolving ability of the system. In addition to the disadvantage of changes in the gross configuration of the DNA, unlike the CHEF system, RGE suffers from the rotational forces which can stress the agarose gel and also from mechanical complexity.

In still another embodiment of PFGE, described by Hood and fellow researchers in Birren, B.W., Lai, E., Clark, S.M., Hood, L. and Simon, M.I. (1988), "Optimized Conditions for Pulsed Field Gel Electrophoretic Separations of DNA," *Nucleic Acids Res.* 16:7563–7582 and Clark, S.M., Lai, E., Birren, B.W. and Hood, L. (1988), "A Novel Instrument for Separating Large DNA Molecules with Pulsed Homogeneous Electric Fields," *Science* 241:1203–1205, a programmable, autonomously controlled electrode gel electrophoresis (PACE) apparatus allows for the control of the electric field parameters. The PACE system includes a buffer tank with 24 independently regulated electrodes allowing the user to control pulse times and electric field angles. However, PACE also includes 24 high voltage amplifiers with 24 identical sets of digital-to-analog converter amplifiers in combination, all controlled by a personal computer.

The PACE apparatus, although versatile, has a disadvantage in that it is costly and its practical use in research labs appears to be limited.

The use of perpendicular pulses of electric fields which are repeated to form a reversing stairstep pattern is reported in Bancroft, I. and Walk, C.P. (1988), "Pulsed Homogenous Orthogonal Field Gel Electrophoresis (PHOGE)," *Nucleic Acids Res.* 15:7405–7418. One field pulse is parallel to the actual direction of migration and other pulses are either 90 degrees to the right or 90 degrees to the left of the direction of migration.

Another prior art technique of significance is a variation of PHOGE and also produces stairsteps from long duration pulses. This technique is described in Schwartz, D. C., and Koval, M. (1989), "Conformational dynamics of individual DNA molecules during gel electrophoresis," *Nature* 338:530–522. It reports the use of alternate perpendicular pulses of 6 to 8-second pulse pair periods, from 3 to 5 seconds for each of the two perpendicular pulse pairs (1/6 to $\frac{1}{8}$ Hz).

With multiple pulse repeats at these low pulse frequencies, DNA bends in a multiple stairstep or staircase-like configuration with a bend each time the field alternates from one perpendicular direction to the other. This is as predicted in Schwartz, D..C. (1985), "Giga-Dalton Sized DNA Molecules," pp. 81–83, doctoral dissertation Columbia University (University Microfilms International).

After a longer period, 80 to 90 seconds, Schwartz and Koval reverse the polarity of one of the pulse fields so that the general trend of the staircase pattern alternates through an angle of 90 or 120 degrees, depending on the ratio of the pulse widths in the pulse pair period. The 80 to 90 second period corresponds to the pulse cycles used by previous workers. The staircase effect results from allowing sufficient time between pulses for gross changes in configuration (generation of the staircase pattern itself), which is what happens in the 8 second perpendicular pulse separation reported by Schwartz and Canter (1984) in the Cell article.

The use of uniform, pulsed perpendicular fields is also reported by Chu et al. and by Bancroft and Wolk (supra). Separation by slow (greater than 1 second) complexly pulsed electrophoresis as reported by Schwartz and Koval does not differ in principle from that described by Schwartz and Canter, Chu and especially by Bancroft and Wolk because all deal with perpendicular changes in field direction followed by enough time for new gross changes in DNA conformation to take place before the next field change. Bancroft and Wolk also use a similar directional change pattern for the electric field.

Each of the prior art pulsed field techniqes has the disadvantage of using a time duration for changing the field pattern that is in the order of a second or longer for separating large DNAs.

In the past, orthogonal pulses of duration too short to allow change in DNA configuration to take place were expected to appear as a vector sum, and be generally useless for separating DNA. This was predicted in Schwartz, D.C. (1985) "Giga-Dalton Sized DNA Molecules," p. 84, doctoral dissertation, Columbia University (University Microfilms International). The utility of such short pulses is a surprising result.

SUMMARY OF THE INVENTION

Accordingly, it is an object of the invention to provide a novel pulsed field DNA electrophoresis technique.

It is a further object of the invention to provide a novel pulsed field DNA electrophoresis apparatus.

It is a still further object of the invention to provide a novel pulsed field DNA electrophoresis technique using a field switching angle which is easily changeable by varying the time duration ratio of a perpendicular and parallel field at a frequency higher than that corresponding to the time for DNA to change its gross configuration under the influence of the field.

It is a still further object of the invention is to provide a novel pulsed field DNA electrophoresis apparatus that: (1) uses a field switching angle which is easily changeable by varying the time duration ratio of a perpendicular and parallel field at a frequency higher than that corresponding to the time for DNA to change its gross configuration under the influence of the field; and (2) does not require an external computer or a matrix of matched or expensive circuits.

It is a still further object of the invention to provide an apparatus which improves the interaction between the DNA being separated and the gel matrix to produce faster separation of very large DNA.

It is a still further object of the invention to provide a low cost, versatile PFGE system for routine laboratory use which permits electric field force, electric field angle and pulse duration to be set.

It is a still further object of the invention to provide novel electrophoresis apparatuses and techniques for resolving DNA molecules greater than 1,000 kb. and result in straight, unbent lanes.

It is a still further object of the invention to provide novel electrophoresis apparatuses and techniques that provide repeated successive orthogonal field pulsing at a first angle perpendicular to and on a first side of an overall direction of migration of the DNA and at a later time reversing to the opposite perpendicular angle on the opposite side of the overall direction of migration.

In accordance with the above and further objects of the invention, a low cost, versatile PFGE system is provided for routine laboratory use that includes means for permitting the adjustability of the electric field force, electric field angle and the pulse duration to resolve DNA molecules greater than 1,000 kb and result in straight, unbent lanes. The means for permitting the adjustability of the electric field force, electric field angle and the pulse duration includes a means for permitting adjustment of at least one of: (1) the pulse durations in a range that maintains the pulse durations shorter than one-tenth of a second; (2) the angle or angles of two fields with respect to each other; (3) the intensity of the fields; and (4) the number of repetitions of pulses of the fields before changing the angle of the two fields with respect to each other.

The straight unbent lanes as used in this description for the path of DNA is meant to distinguish movement of the strand of DNA that results in overall movement of the chromosome or fragment itself rather than changes in conformal position of different bases with respect to each other.

The words, "an unbent lane", in this specification, mean the DNA does not move substantially at an angle to the overall direction of movement so that during ten centimeters of movement with respect to the gel, the DNA does not move at an angle greater than 5 degrees to the overall motion of the DNA for a continuous distance of more than one-half centimeter nor deviate from the overall direction of movement by more than one-half centimeter measured perpendicular to the direction of movement. The terminology "no change in gross configuration" or "without change in gross configuration" or "no significant conformational change" or "no substantial flexural bending" means in this specification that the respective portions of the DNA retain their respective geometric orientation with respect to a previous observation with no more than 1 micrometer of such portions deviating by more than 40 degrees, nor 2 micrometers of such portions deviating by more than 70 degrees. In these definitions, the time is between the previous observation and the observation in question. An instrumental criterion for forces or pulses that do not cause significant conformal change nor bent lanes is that the DNA should not migrate more than two pore diameters of the supporting medium during a single pulse. This is 0.4 micrometer for some agarose gels. By "stiff rod" or "stiff" is meant no tendency for the DNA molecules to undergo significant conformational change during a pulse period or a series of pulse periods during which it migrates along an unbent lane inspite of collisions with particles in the gel. Many of the terms in this specification are consistent with the terminology provided in volumes 1, 2 and 3 of *Biophysical Chemistry*, by Cantor and Schimmel, W.H. Freeman and Company, N.Y., N.Y., U.S.A., the disclosure of which is incorporated herein by reference.

In using the apparatus, the electric field parameters adjusted in a manner specific for the DNA size range to be resolved and are preset to prevent angular lanes of migration of the DNA.

As can be understood from the above description, the electrophoresis apparatus of this invention has several advantages, such as for example: (1) it is relatively uncomplex and inexpensive; (2) it is able to separate DNA constituting large chromosome segments; (3) it does not result in bent or curved lanes of travel of the DNA; (4) it is versatile in handling different sizes of DNA strands; and (5) the internal electronic design which provides for this versatility does not require an external computer or a matrix of matched or expensive circuits. Thus, its cost is much lower than the PACE system.

SUMMARY OF THE DRAWINGS

The above noted and other features of the invention will be better understood from the following detailed description when read in connection with the drawings, in which.

DETAILED DESCRIPTION

Figure 1:
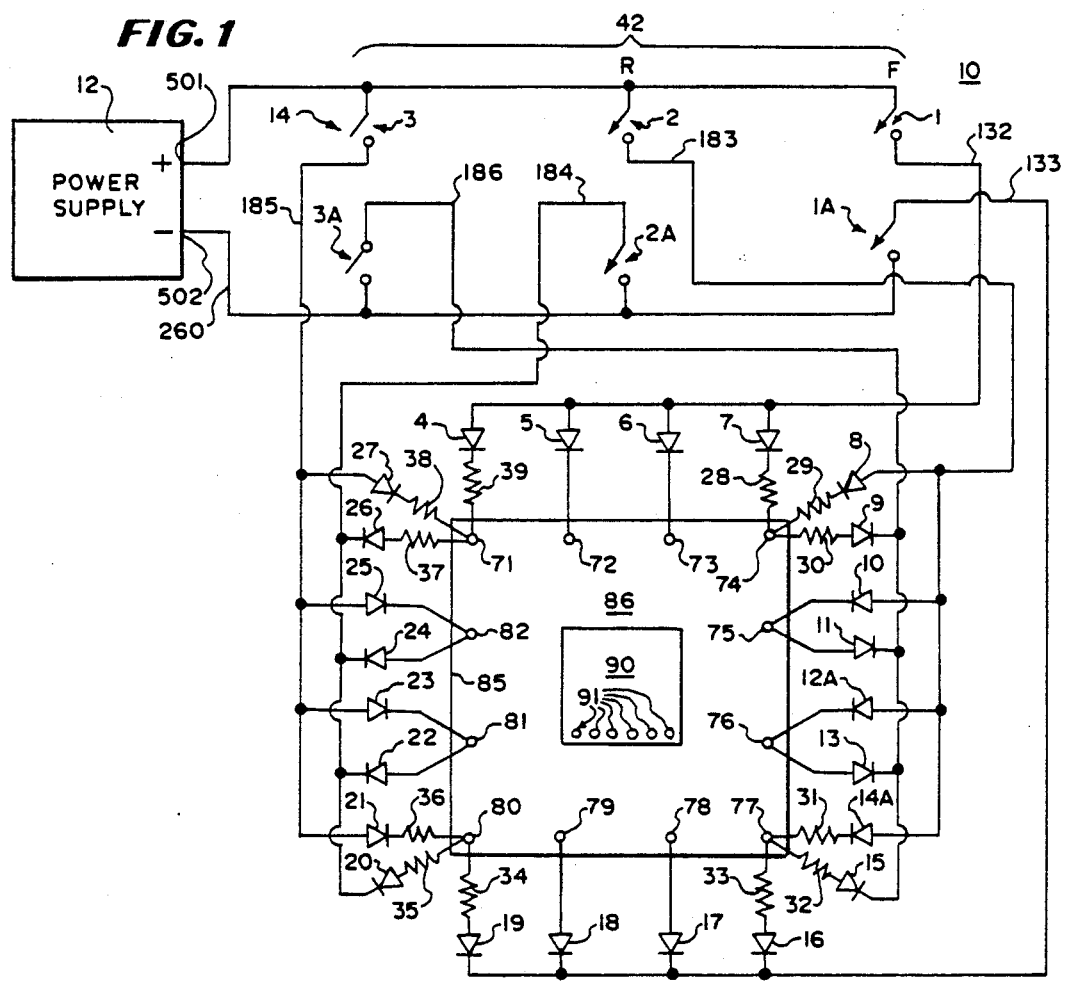
FIG. 1 is an overall schematic of a gel electrophoresis apparatus according to an embodiment of the invention.

In FIG. 1, there is shown a simplified schematic drawing of electrophoresis apparatus 10 having a power supply 12, an electrophoresis gel system including the tank 85 and an adjustable switching means 42 connected together for controlling the electric field force, electric field angle and the pulse duration to resolve DNA molecules greater than 1,000 kb in length along straight, unbent lanes within a gel. The electrophoresis system 10 permits adjustment of the pulse durations through a range from generally one-tenth of a second to shorter ranges.

The electrophoresis gel system includes the shallow electrophoresis tank 85 which is made out of insulating material adapted to contain electrolyte buffer 86. Completely submerged in this buffer is a square sheet of agarose gel 90 containing a number of wells or oval depressions 91. In these wells are plugs of gel containing mixed DNA to be separated.

To create the field in the gel separating system, electrodes 71 through 82 provide electrical contact to the buffer from the power supply 12 through the switching means 42. The electrodes are preferably made of an inert metal such as platinum.

To provide switching of the fields, the switching means 42 includes high-speed switching diodes 4 through 27, resistors 28-39 and adjustable means 14 that connect the electrodes through switching 42 to the direct current power supply 12. The adjustable means 14 includes three sets of switches 1, 1A; 2,2A and 3,3A.

To prevent interference between current paths, the diodes 4-27 are connected in three sets: (1) diodes 4 to 7 having their anodes connected to switch 1 and thence to the positive terminal 501 of the power supply 12; and diodes 16 through 19 having their cathodes connected to switch 1A and thence to the negative terminal 502 of the power supply 12; (2) diodes 8, 10, 12A, and 14A having their anodes connected to switch 2 and thence to the positive terminal 501; and diodes 20, 22, 24 and 26 having their cathodes connected to switch 2A and thence to the negative terminal 502; and (3) diodes 21, 23, 25 and 27 having their anodes connected to switch 3 and from there to the positive terminal 501 and diodes 9, 11, 13 and 15 having their anodes connected to switch 3A and from there to the negative terminal 502.

The electrode 71 is electrically connected to the cathodes of the diodes 4 and 27 through corresponding ones of the resistors 38 and 39 and to the anode of diode 26 through the resistor 37; the electrode 74 is electrically connected to the cathodes of the diodes 7 and 8 through corresponding ones of the resistors 28 and 29 and to the anode of diode 9 through the resistor 30; the electrode 77 is electrically connected to the cathodes of the diodes 14A and 15 through corresponding ones of the resistors 31 and 32 and to the anode of diode 16 through the resistor 33; the electrode 80 is electrically connected to the anodes of the diodes 19 and 20 through corresponding ones of the resistors 34 and 35 and to the cathode of diode 21 through the resistor 36. The cathodes of diodes 5, 6, 10, 12A, 23 and 25 are electrically connected to respective ones of the electrodes 72, 73, 75, 76, 81, and 82 and the anodes of diodes 11, 12A, 17, 18, 22 and 24 are electrically connected to respective ones of the electrodes 75, 76, 78, 79, 81 and 82.

The diodes 4-27 prevent the circuits energized by switches 3-3A, switches 2-2A and switches 1-1A from interfering with each other since only one of these three switch pairs is closed at any given time and since a closed pair is always opened before the next open pair is closed. Resistors 28 through 39 limit the amount of reverse recovery current through the diodes when the switches are transferred.

Before operating the embodiment of FIG. 1, mixture of large DNA molecules are inserted into the wells 91 of the gel 90. The angle and rate of change of the angle of the fields and the pulse durations are selected in accordance with the segments of DNA that are to be separated. Other variables may play a role in this selection such as field intensity, the number of pulses between direction changes and the overall duty factor, or relative percentage of time that either of the two pulses is on, compared to the duration of the entire two-pulse cycle.

In the operation of the embodiment of FIG. 1, when switches 1,1A are closed, electrodes 71 through 74 are connected to the positive terminal of the power supply and electrodes 77 through 80 are connected to the negative terminal of the power supply. This establishes an electric field within the buffer 86 located within the tank 85.

Since the buffer covers the agarose gel 90, the electric field is also established in the gel. Under the influence of the field, negatively charged DNA starts to migrate out of the wells toward the positive electrodes, 71, 72, 73, 74.

After a very short period of time switches 1,1A open, followed by the closure of switches 2,2A. This establishes a positive potential on electrodes 74, 75, 76, and 77 through the diodes connected to switch 2A. This causes the DNA to migrate to the right. This cycle repeats very rapidly. This cycle repetition frequency is greater than 10 hertz, so the large DNA molecule does not have time to change its gross configuration during any one pulse cycle and preferably moves with a true average direction of migration as it moves with an average migration vector at an angle between horizontal movement to the right and vertical movement toward the top of the figure.

After a more extended period of time, usually after more than 100 of such foregoing switch cycles have taken place, switching action stops between switches 1–1A and switches 2–2A. It immediately resumes with similar switching between switches 3–3A and switches 1–1A. When switches 3 and 3A close, positive potential from the power supply is applied to electrodes 80 through 82 and electrode 71 through diodes 21, 23, 24, and 27. Negative power supply potential is supplied through switch 3A to diodes 9, 11, 13 and 15 to electrodes 74 through 77.

When switches 3 and 3A are closed, electrodes 74 through 77 carry a negative potential and electrodes 80, 81, 82 and 71 carry a positive potential. This causes negatively charged DNA to migrate slightly or tend to migrate to the left.

A short time after switches 3–3A are closed, these two switches reopen and switches 1 and 1A close establishing a field which causes DNA to move vertically toward the top of the figure. Switches 3–3A and 1–1A alternate closing and opening very rapidly, with each switch pair opening before the other switch pair closes so that the field is uniform and applied across only one direction at a time. As earlier, this is done at a frequency greater than 10 hertz so that gross changes in DNA configuration do not occur during the switching cycle between switches 1–1A and 3–3A. However, the period of repeated alternation between switches 1–1A and 2–2A on one hand and repeated alternation between switches 3–3A and switches 1–1A on the other hand is much slower.

Preferably, more than 100 cycles of alternation between switches 1–1A and 2–2A occur before operation transfers to the alternation between switches 3–3A and 1–1A. Conversely also at least 100 alternations between stitches 3–3A and 1–1A occur before operation transfers back to alternation between switches 1–1A and 2–2A. This overall cycle repeats many times during the DNA separation process. Furthermore the time pulse durations of the 1-2 alternation should be substantially equal to the time durations of the 3-1 alternation to obtain straight and well-aligned separation lanes.

Successful DNA separations with the subject invention have been made with alternation frequencies from 10 hertz to 50 kilohertz and horizontal field reversal times of from 20 seconds field trending to the right followed by 20 seconds field trending to the left followed by 20 seconds field trending to the right, and so on, on up to substantially longer times. At times on the order of 200 seconds and at alternating frequencies of 50 KHz, whole chromosomes from yeast species *S. Cerevisiae* (200 to 3000 kb) and *S. pombe* (3000 to 6000 kb) have been separated.

The electrophoresis tank 85 shown in FIG. 1 is drawn in a simplified form to illustrate the principle without confusing complexity in the diagram. In a preferred embodiment: (1) the tank is 20 cm square inside; (2) the agarose gel 90 is 10 cm square by about 4 mm thick, is located in the center of the tank and is completely immersed in the buffer 86 to a depth such that its top surface is at least 1 mm under the surface of the buffer.

Instead of four electrodes on each side of the tank, eight electrodes are used to make the electric field within the buffer more uniform. All electrodes are wired as shown in the figure. There are of course still only four sets of three diodes, one set connected to each of the four corner electrodes in the tank. However, there are six intermediate electrodes on each of the four sides of the tank between the corner electrodes. They are wired exactly as shown for each of the four sets of the two side electrodes in the figure.

Since alternation frequencies in excess of 50 kilohertz are useful with this appartus, the diodes 4 through 27 are high frequency, fast-switching diodes such as Amperex Type BYV26C diodes as well as Amperex BAV21 diodes. The former diode is a 600 volt rated diode and only a single diode needs to be used for each diode position indicated in FIG. 1.

Since the reverse voltage rating of the BAV21 diode currently being used is only 200 volts, three diodes are used in series in each of the diode positions shown in FIG. 1. Voltage ratings as high as 600 volts are not strictly necessary for use on the relatively small 20 cm square tank used for electrophoresing 10 cm square gels. However the power supply 12 and switching arrangement 42 are designed to handle larger gels residing in larger gel tanks and therefore are capable of providing voltages to the tank and its diodes; a voltage somewhat in excess of 500 volts. Therefore high voltage diodes are used in this embodiment in the interest of reliability and safety. It is expected that other embodiments will utilize larger gels in larger tanks or narrower pulses (smaller overall duty factors) with the same size gels and require such high voltage diodes.

Figure 2:
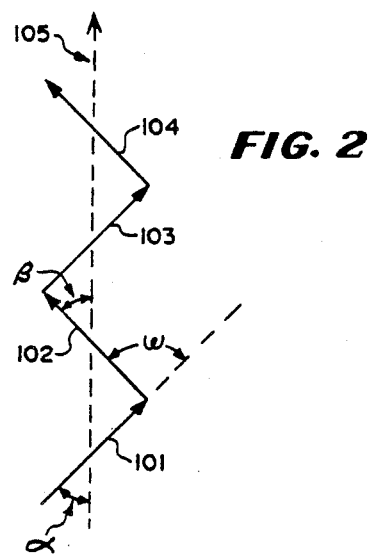
FIG. 2 is a schematic fragmentary view within a electrophoresis gel illustrating the vector direction of the fields and the path that would be taken by DNA in many PFGE systems.

In FIG. 2 there is shown an exposition of the path of the DNA molecule as it migrates in the gel 90 (FIG. 1) having a general direction of migration indicated at 105, and several vectors of motion shown at 101–104 for illustration purposes.

To obtain the overall direction of migration 105, several angled migration vectors are alternately created in directions which results in the overall migration direction. As shown in FIG. 2, one of these migration vectors, vector 101, is formed from a series of pulses caused by the rapid opening and closing of switches 1–1A and 2–2A alternately as described in connection with FIG. 1.

As the DNA molecule migrates along this vector, its configuration changes as it hooks and tumbles along as described by Smith, et al. in Smith, S.B., Aldridge, P.K., and Calles, J.B. (1989) "Observation of Individual DNA Molecules Undergoing Gel Electrophoresis," *Science* 243:203–206. The frequency of alternation between switchings is high enough so that the migration behaves substantially as if the field were continuous.

At the arrowhead end of migration vector 101, switches 1–1A stop alternating with switches 2–2A, and switches 3–3A begin alternating rapidly with switches 1–1A. This changes the DNA's migration to the migration vector labeled 102. Again the alternation frequency is high enough so that the DNA molecule migrates substantially as if it were in a continuous field when moving along vector 102.

After a selected period of time of migration along vector 102, equal to the time of migration along vector 101, the alternation sequence changes back to that that took place from migration vector 101 formed by the rapid alternation between closures of switches 1–1A and 2–2A During this time, the large DNA molecule moves along vector 103 in a manner similar to that as if it were in a continuous field rather than a perpendicularly pulsing field. A further reversal takes place at the arrowhead end of vector 103 and migration continues along vector 104, etc. The resulting overall migration is upwards along the average path 105.

The effect from switching from vector 101 to vector 102, from vector 102 to 103 and from vector 103 to 104, on so one is to provide differentially lower mobility for large DNA compared to small DNA. It is this slow, overall obtuse angle change in migration vector which provides differential mobility necessary for the separation of large DNA's. The relative enhancement of DNA-gel interaction due to the submicroscopically vibrating direction of migration during pulsing is believed to enhance this differential by increasing the sieving effect in a manner related to the size of the molecule in addition to the time spent realigning the molecule due to horizontal field reversal. The stability of the gross configuration during one pulse cycle is believed to further enhance this effect. It is believed that these enhancement effects account for faster resolution of large DNA. The movement of the large DNA strand is in an unbent lane of movement 105. The words, "an unbent lane", in this specification, mean the DNA does not move substantially at an angle to the overall direction of movement so that during ten centimeters of movement with respect to the gel, the DNA does not move at an angle greater than 5 degrees to the overall motion of the DNA for a continuous distance of more than one-half centimeter nor deviate from the overall direction of movement by more than one-half centimeter measured perpendicular to the direction of movement. The terminology "no change in gross configuration" or "without change in gross configuration" or "no significant conformational change" or "no substantial flexural bending" means in this specification that the respective portions of the DNA retain their respective geometric orientation with respect to a previous observation with no more than 1 micrometer of such portions deviating by more than 40 degrees, nor 2 micrometers of such portions deviating by more than 70 degrees. In these definitions, the time is between the previous observation and the observation in question. An instrumental criterion for forces or pulses that do not cause significant conformal change nor bent lanes is that the DNA should not migrate more than two pore diameters of the supporting medium during a single pulse. This is 0.4 micrometer for some agarose gels. By "stiff rod" or "stiff" is meant no tendency for the DNA molecules to undergo significant conformational change during a pulse period or a series of pulse periods during which it migrates along an unbent lane inspite of collisions with particles in the gel. Many of the terms in this specification are consistent with the terminology provided in volumes 1, 2 and 3 of *Biophysical Chemistry*, by Cantor and Schimmel, W.H. Freeman and Company, N.Y., N.Y., U.S.A., the disclosure of which is incorporated herein by reference.

In the subject invention, a large number (preferably over 100) 90-degree field alternations take place to form each field migration vector and the 90-degree alternations forming the migration vector take place at a frequency greater than 10 hertz. Migration vector 101 is inclined by the angle alpha to the direction of overall migration 105. Migration vector 102 is inclined by the angle beta to the direction of overall migration 105. Migration vector 102 makes an angle of omega with respect to vector 101.

Angle omega is equal to the sum of angle alpha plus angle beta. The angle alpha of vector 101 is equal to the angle beta of vector 102 since the relative time durations of the switching of switches 1-1A and 2-2A are the same as that for switches 3-3A and 1-1A. Since angle alpha equals angle beta, the angle omega is equal to two times angle (alpha or beta). It is usually preferable to operate with an angle omega equal to about 120 degrees.

While perpendicular fields are used in the preferred embodiment, other fields acting at angles to each other may be used provided the pulses do not change the overall DNA configuration, the time between pulses does not relax (allow time to change the configuration of) the DNA, the changes in direction of the pulses or polarity of the fields does not unduly bend the lane, and the resultant does not unduly bend the lane, and the resultant motion is along a predictable lane permitting comparisons between lanes. Moreover, the pulses in the orthogonal fields or fields that are at angle to each other need not alternate on a one-to-one basis but other ratios may be used such as two pulses perpendicular to the direction of migration to each pulse at an angle along the direction of migration.

The frequencies of pulses to be used and the periods of time between reversals of polarity of the angled fields may be selected more carefully for individual cases by trial in error since the values and ranges given herein were selected because of results on only some tests with certain DNA strands.

Figure 3:
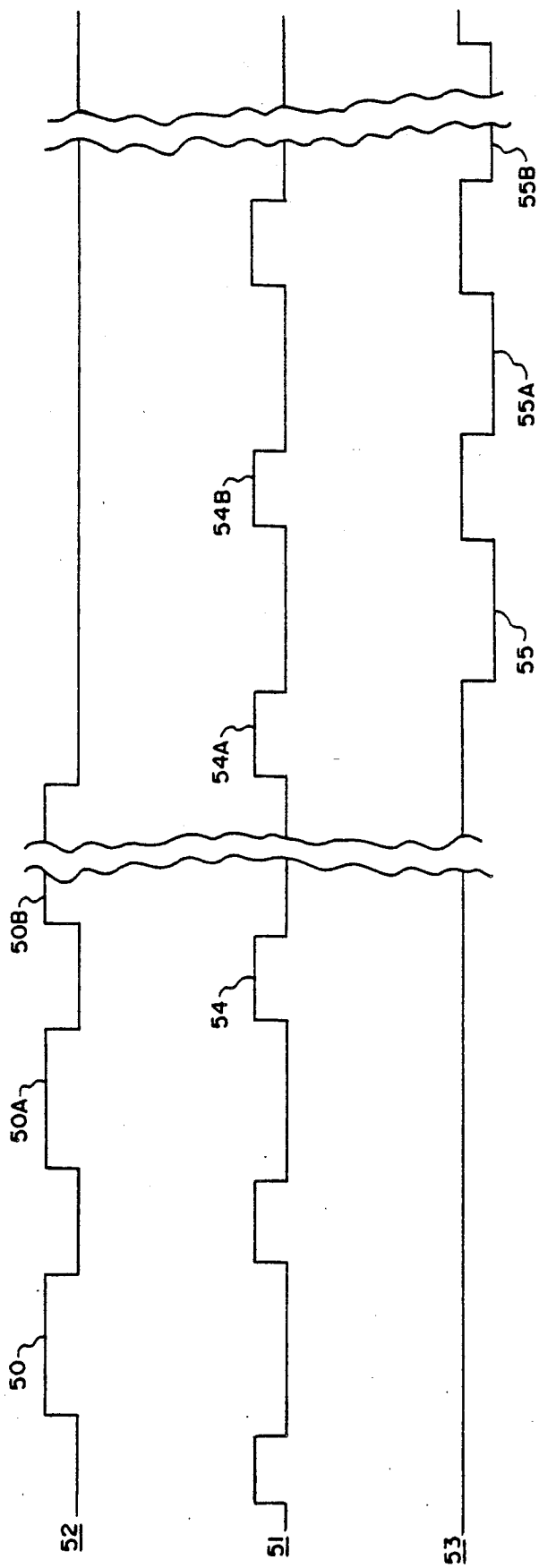
FIG. 3 illustrates the pulsed timing of voltages applied to an electrophoresis tank in accordance with the embodiment of FIG. 1.
Figure 5:
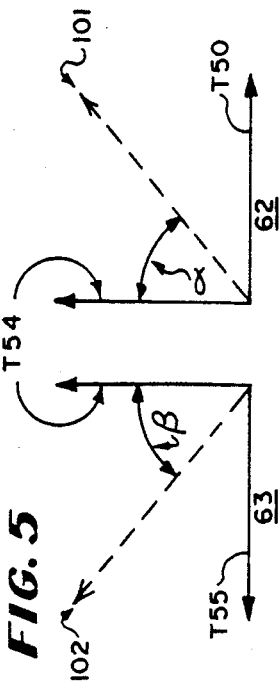
FIG. 5 represents variable angle migration vectors generated by two perpendicular, time shared fields in accordance with an embodiment of the invention.
Figure 4:
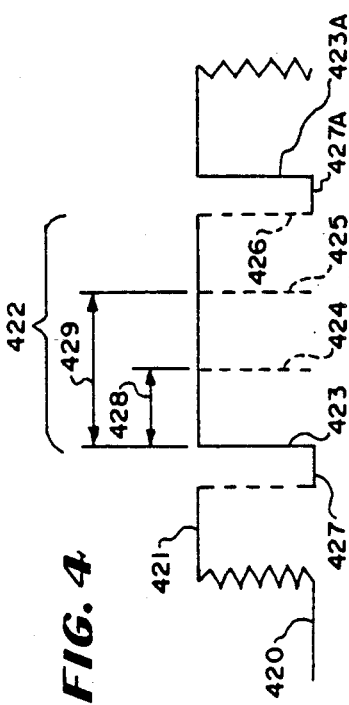
FIG. 4 illustrates relative pulse duration or duty factor of a pulse generator used to generate the pulses of FIG. 3.

In FIG. 3, FIG. 4 and FIG. 5, there are shown diagrams illustrating the manner in which the angle of migration is varied using the method of the invention. In FIG. 3, there is shown a graph of field intensity against time having ordinates of intensity and abscissae of time illustrating the relationship of the timing of the switch closures in the switching device 42, which are curves of: (1) switching a pattern 51 corresponding to the time of the closing and opening of switch pair 1-1A; (2) switching pattern 52 corresponding to the time of the opening and closing of switch pair 2-2A; and switching pattern 52 corresponding to the timing of the opening and closing of switch 3-3A.

In curves 51 and 52 in FIG. 3., the pulses 54, 54A, and 54B represent closure time of switch pair 1,1A; and 50, 50A, 50B represent closure times of switch pair 2-2A. The switch closures alternate in time as shown at 51 and 52, with a short duration of time (for example, in the low microsecond region) between stitch closures, during which time all switches are open so that no set of switches from a given side are closed at the time of switches from another side and the field is always in one direction. The field is alternately along the general overall direction of migration 105 and from an angle to the direction of migration. This switching pattern produces a migration vector at a rightwards angle (101 in FIG. 2). Switch 3-3A stay open during this migration at a rightwards angle.

Switch 2-2A open and stays open during horizontal field reversal for migration at a leftwards angle. This migration entails the alternation of closures between switch pairs 3-3A and 1-1A is shown in FIG. 3 at 51 and 53. Switch pair 3-3A is connected to provide opposite field polarity in electrophoresis tank 85 compared to switch pair 2-2A. Therefore the polarity of the pulses shown at 53 are inverted, producing a DNA migration vector at a leftwards angle (102 in FIG. 1A) instead of a rightwards angle.

The closure durations of switch pair 3-3A are shown as 55, 55A, 55B and switch pair 1-1A is open at these times. Closure durations of switch pair 1-1A are shown as 54, 54A, 54B, and switch pair 3–3A is open at these times. As was the case for switch pairs 1–1A and 2–2A, there is a short period of time, on the order of microseconds, after the time one pair of switches 1–1A and 3–3A opens, before the other pair of switches closes. This time is kept sufficiently short to ensure that there are no configurational changes of the DNA between pulses. The time between pulses depends on the size of the DNA strand but generally should be less than one second and more commonly are in the microsecond range.

The angle omega, which is the angle between one migration vector to the next, is changed by varying: (1) the ratio between pulse lengths 50 and 54; and (2) the ratio between pulse lengths 55 and 54. These two ratios are generally equal and pulse length 50 is kept equal to pulse length 55. This is controlled by a variable-duty factor pulse generator whose output is shown in FIG. 4.

In FIG. 4, there is shown the output of this pulse generator, having two states: a low state 420 and a high state 421. The pulse generator operates continuously and repetitively with the pulse cycle shown as 422. The pulse starts from low and rises or goes high as indicated at 423.

The pulse generator is set or programmed to any constant frequency between 10 hertz and 1 megahertz. By means of an adjustable duty factor setting, it produces a more or less infinitely variable pulse time width percentage which width can be set from substantially zero to the period of one cycle of the pulse generator frequency. Pulse falls indicated as 424, 425 and 426 indicate three of the many possible pulse durations. The pulse fall at 424 produces the pulse duration 428, a pulse fall at 425 produces the pulse generation 429, and so forth. Due to limitations in the pulse generator it may not be possible to attain an output that is continuously high as indicated at 421.

Between pulse cycles there may be a short period of low voltage such as 427 and 427A. Commercially pulse generator circuits are available in which this "dead time" is so small as to be negligible for the purposes of the invention. The pulse output of FIG. 4 is used to generate the pulse pattern of FIG. 3.

When the output is high as shown at 421 one of switch pairs 2–2A or 3–3A is closed and switch 1–1A is opened so that the instantaneous electric field is perpendicular to the overall direction of migration. When the output the pulse generator is low as shown at 420, both switch pairs 2–2A and 3–3A are turned off and switch pair 1–1A is turned on, producing a field such as 54 parallel to the overall direction of migration. The setting of the angle is determined by the duty factor of the pulse timing: the ratio time for which pulses 50, 50A, 50B or pulses 55, 55A, 55B are "on" compared to the time that pulses 54, 54A, 54B are "on". This is illustrated in FIG. 5.

In FIG. 5 there are shown two two-dimensional vector diagrams relating to the pulse duration relationships existing between 51 and 52 (diagram 62), and between 51 and 53 (diagram 63). In diagram 62, the length of vector T50 corresponds to the relative time duration of pulses 50, 50A, 50B and the length of vector T54 corresponds to the relative time duration of the pulses 54, 54A, 54B. In diagram 63, vector T55 corresponds to the time duration of pulses 55, 55A, 55B and vector T54 is the same as in diagram 62.

If there are no significant changes in DNA configuration between a pulse period composed of pulses 50 and 54, there will be no change in electrophoretic mobility over the pulse cycle. The conformational changes due to conventional pulse duration patterns affect short term electrophoretic mobility. However it has been discovered that if the pulses are fast enough, unprecidentally fast for gel electrophoresis of large DNA, there is no gross change in DNA configuration during the pulse cycle and no significant change in mobility during the pulse cycle.

With the mobility being constant over the pulse period, migration may be treated as a linear, time-invariant system, and the resultant migration vector for rapid pulse alterations repeated numerous enough times may be treated as the two-dimension vector sum of the relative pulse durations. This is indicated as the migration vector 101 shown in vector diagram 62 of FIG. 5. The vector component T50 corresponds to the relative time in which the field is perpendicular to the direction of migration, with migration to the right in the gel 90. The angle alpha in diagram 62 corresponds to the angle alpha in FIG. 2. The vector component T55 (diagram 63) is equal and opposite to vector component T50, so the perpendicular directions cancel with respect to the path of the lane in the overall DNA separation. The direction T54 is the overall direction of migration (105 in FIG. 2).

Diagram 63 shows time durations T54 and T55 used as component vectors to generate the migration vector 102. As with diagram 62, this is only correct if the switching frequency between the pulses 54 (FIG. 3) and 50 or 55 are fast enough so that there are significant configurational changes in the DNA during the pulse cycle.

If the slow alteration period described by Schwartz, D.C., and Kovel, M. (1989), "Conformational Dynamics of Individual DNA Molecules Gel Electrophoresis," *Nature* 338:520–522 were used, it would be difficult to define vectors 101 and 102 since electrophoretic mobility would not be constant during the pulse alternation cycle due to conformational changes of the DNA. Under the influence of a suddenly applied electric field, the DNA develops conformational change over a period of time. The instantaneous mobility depends upon conformation change which increases with both field and time.

If the DNA is in a field which is perpendicularly pulsed repeatedly and relatively slowly (on the order of seconds) the conformation differs significantly between the beginning and end of each pulse. This will not be a self-cancelling effect since the perpendicular pulse pattern is repeated over a number of identical cycles. Mobility will be time and voltage dependent and a true migration vector cannot be developed.

Operation at sufficiently high frequencies (greater than ca. 3 kilohertz) tends to suppress even minor effects of the instantaneous field on the DNA such as flexural bending due to electrostatic induction of dipoles in the DNA. Above 3 kilohertz the relaxation time ("time constant") of movement of even a segment of DNA so short that it behaves somewhat like a stiff rod and tends to be slower than the period of field alternation.

At such high frequencies, the viscous friction of the buffer within the surrounding pores of the agarose gel opposes bending of the DNA, even on a minute scale, as the perpendicular field alternates. Since the length of a DNA segment that acts stiff is about 60 nanometers, and the pore size in agarose gels is about 150 nanometers, varying the pulse frequency above or below 3 kilohertz can advantageously affect the separation by varying the DNA/gel interaction.

As shown in FIG. 5, the angles alpha and beta are each equal to the arctangent of the time period of the perpendicular field multiplied by the voltage at that time, divided by the time period of the horizontal field multiplied by the voltage at that time. The time period is multiplied by the pulse voltage because the DNA movement is the product of the two with high frequencies since there is no significant conformational changes in the DNA during each pulse. Accordingly, the DNA mobility is constant over the pulse cycle. If the pulse voltage is constant, as in a preferred embodiment, its effect cancels out with respect to the angles alpha and beta.

Since the angle omega (FIG. 2) equals alpha plus beta, omega equals two times the arctangent of the time of one horizontal pulse divided by the time of one pulse in the direction of overall migtation. Thus, the angle omega can be set from essentially zero up to 180 degrees by varying the duty factor of a pulse generator to produce variable width pulses as illustrated in FIG. 4.

Figure 6A:
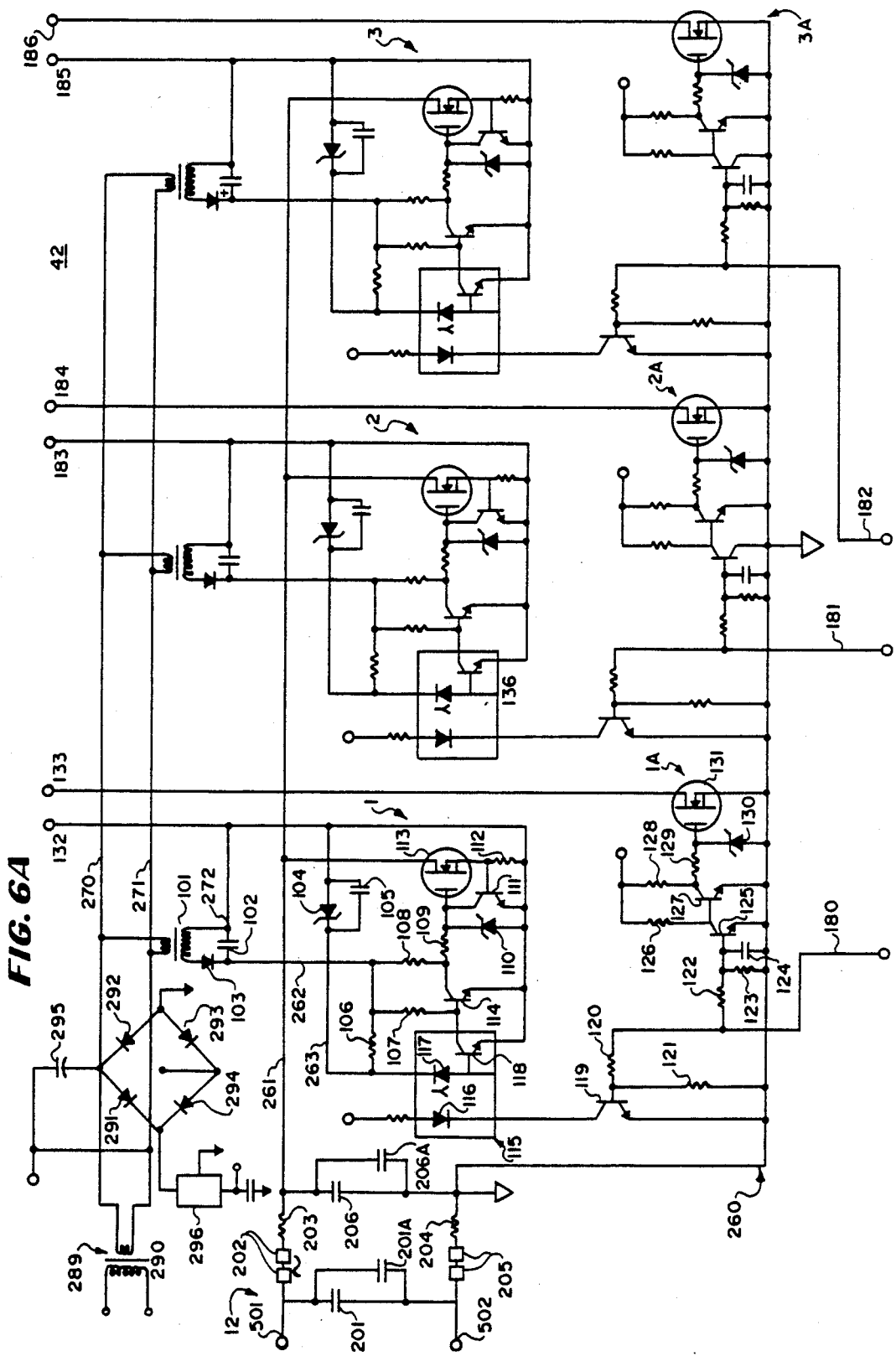
FIGS. 6A and 6B are a schematic diagram of switching arrangement shown in simplified form on FIG. 1.
Figure 6B:
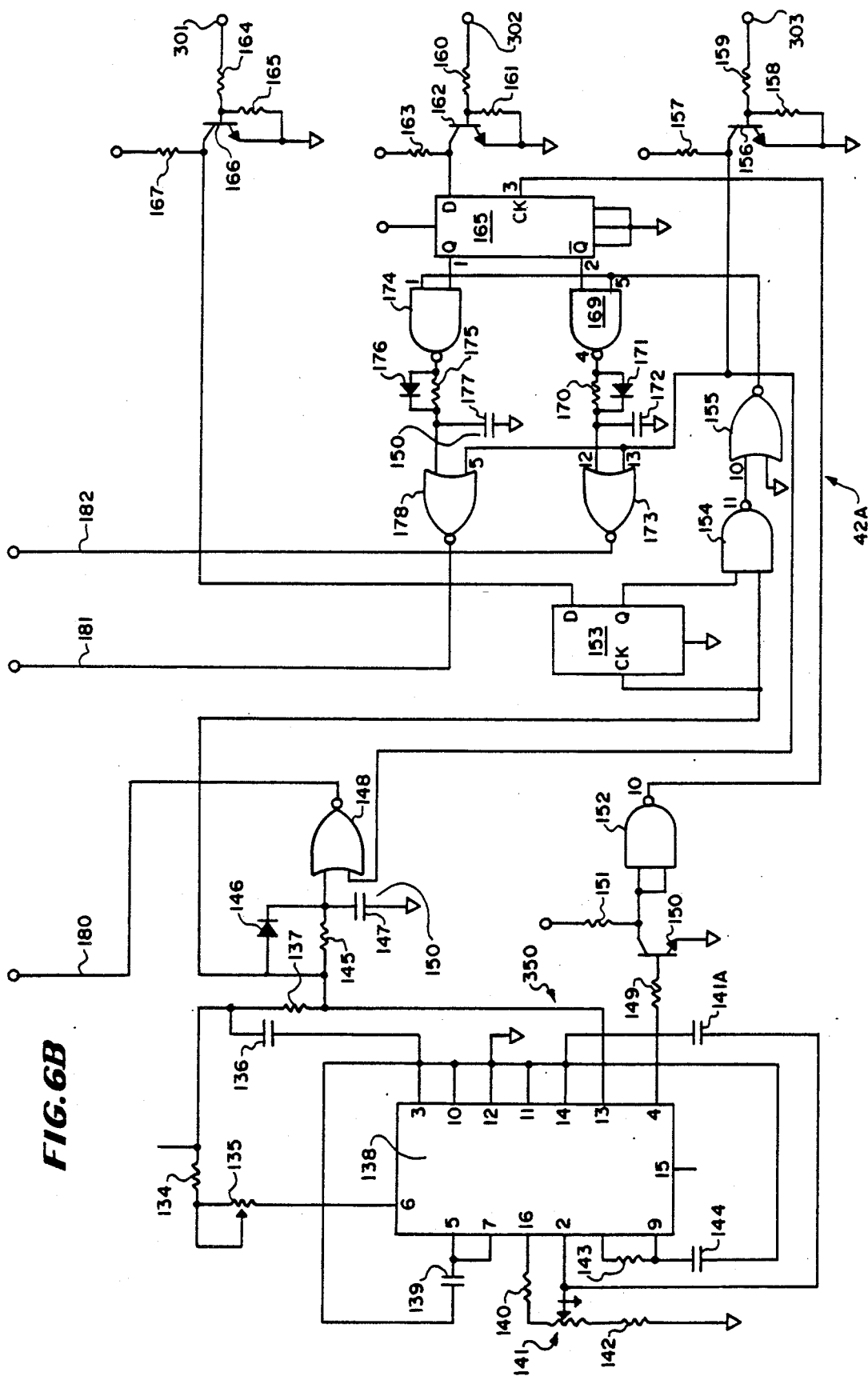

In FIGS. 6A and 6B, there is shown an electrical schematic drawing of the switching mechanism indicated as 42 in FIG. 1 having pulse generator integrated circuit 138 and its ancillary pulse generator circuitry; logic circuitry 42A and switching circuitry 42 with the switches themselves indicated as 1,1A; 2,2A and 3,3A. The logic circuitry is made of CMOS NAND gates type 4011B, NOR gates type 4001B, D flip-flops type 4013B plus ancillary discrete logic circuitry.

The variable width pulse generator 138 produces continuously variable duty factor from 0 percent to almost 100 percent at a frequency that may be selected between 10 hertz to over 100 kilohertz and is a Silicon General integrated circuit Type 3525A used in a circuit taken from applications literature provided by that company.

In this circuit, capacitor 139 determines the general frequency range selectable by variable resistance 135 in series with the fixed 4.7 K resistor 134. A wide range of pulse frequencies may be selected with a conventional switch (not shown) for selecting different values for capacitor 139 to cover the 10 hertz to over 100 kilohertz frequency range for creating the field alternation rates useful for this apparatus in a manner known in the art. For example, with a 0.0022 microfarad capacitor for 139, a 100 K ohm variable resistor for 135 and a 4.7 K ohm resistor for 134, a frequency range of about 5 to 100 kilohertz results from adjusting the value of variable resistor 135. A 0.044 microfarad capacitor provides a frequency range of 250 hertz to 5 kilohertz, etc. The frequency corresponds to the period (50+54) or (55×54) in FIG. 3, the frequency of one complete perpendicular switching cycle of the fields.

To set the duty factor of the pulse generator's output pulse, a ten-turn potentiometer 141 is connected in series with 301 ohm and 500 ohm of the integrated circuit 138. The 1 K resistor 143 and 0.047 capacitor 144 provide stability compensation for the error amplifier in integrated circuit 138 and the 0.1 microfarad capacitor 141A bypasses noise from the duty factor setting input at pin 2.

The output from the pulse generator integrated circuit is taken from pin 13 so as to provide a 0 to almost 100 percent duty factor instead of a 0 to 50 percent duty factor available from other outputs. This 0 to almost 100 percent output is on lead 350 which is supplied with pullup resistor 137 to raise lead 350 to a high (+15 volts) logic level when current does not flow into pulse generator 138 through pin 13. When current flows through pin 13, this pulls potential on lead 350 to a low logical level near 0 volts.

To control the field in the electrophoresis tank 85 (FIG. 1), the control inputs 301, 302 and 303 are connected so that: (1) control input 303 turns the field in the electrophoresis tank on and off; (2) a conventional switch (not shown) is connected between circuit 303 and the +15 volt supply for the user to turn the field on and off; and (3) a conventional, programmable or adjustable, repeating interval timer, which may be any of the types used in the aforementioned publications by Cantor, Schwartz, Carle, Gardiner, Chu or Hood, the disclosures of which are incorporated herein by reference, is connected to terminal 302 to control the longer-time durations of the migration vectors (101, 102 in FIG. 2). This timer has a fixed 50 percent duty factor.

A conventional switch (not shown) is connected between terminal 301 and +15 volts. When this switch is closed, the field perpendicular to the direction of overall migration is switched off and only the field parallel to this direction is left on. This is a diagnostic feature intended for investigation of migration properties during experimental use or evaluation of the apparatus.

When terminal 303 is at a logical high voltage, the collector of transistor 156 is low, pulling low: the pin 5 input of switch-controlling NOR gate 178, the pin 12 input of switch-controlling NOR gate 173 and the pin 2 input of switch-controlling NOR gate 148. This enables these three NOR gates to turn on the respective switch pairs 2-2A, 3-3A and 1-1A. The NOR gates are types 4001B.

Each of the switch pairs 1-1A, 2-2B and 3-3B, three sets of switches, driving gates and related circuits are identical and operate in an identical manner. Thus only switch-controlling NOR gate 148 and switch pair 1-1A, will be described in detail.

In switch pair 1-1A, the switch elements 1 and 1A themselves are n-channel MOSFET enhancement-mode power transistors, Motorola Type MTP1N60. This transistor was selected because it is capable of handling up to 600 volts and 1 ampere, more than sufficient for the application. It is not desirable to use a higher current transistor for this application, even apart from cost, because the higher gate capacitance of a larger transistor makes submicrosecond switching times difficult. The transistors are indicated as 113 and 131 in the FIG. 6A. The drain of transistor 113 is connected through lead 261 to the positive terminal 501 of power supply 12 (FIGS. 1 and 6A).

The power supply 12 is decoupled by switching transient suppressor elements comprising 0.05 microfarad, 600 volt capacitors 201, 201A, 206 and 206A, ferrite beads 202 and 205, and 4.7 ohm resistors 203 and 204. These filter elements prevent switching transients from transistors 113 and 131 (or any of the other MOSFETs) from disturbing the regulation of power supply 12. Transistor 131 has its source connected to common potential lead 260. This makes its gate drive circuit simple as the gate drive circuit may also be referenced to common potential. However, transisitor 113 has its source connected through current limiting resistor 112 to the positive parallel direction field output terminal and lead 132 (FIGS. 1 and 6A). The voltage at this terminal changes very rapidly and frequently as the apparatus operates and therefore the gate drive for this MOSFET transistor must be isolated.

To this end, a Type 6N136 optoisolator 115 has been used as shown in FIG. 6A to isolate the gate drive of transistor 113 from the logic circuitry. The 6N136 optoisolator's isolation of rapid voltage changes between its input light emitting diode 116 and its output circuitry 117 and 118 is limited by internal capacitance effects. A 6N136 optoisolator is useful only for power supply (12) voltages up to about 200 volts because of the fast switching speeds used.

The preferred embodiment uses a Hewlett-Packard HCPL-2400 optiosolator which has much better such "dv/dt" (high speed, high switching voltage) isolation. The HCPL-2400 is wired slightly differently from that shown in FIG. 6A, as indicated in Hewlett-Packard optoisolation product literature.

When the pulse output lead 350 from the pulse generator 138 goes high, capacitor 147 charges very rapidly (much faster than one microsecond) through diode 146. The rise in potential on pin 1 of NOR gate 148 brings its output lead 180 low. This quickly turns off transistor 119 by removing the supply of base current through resistor 120. With collector current no longer flowing through transistor 119, light emitting diode 116 in optoisolator 115 turns off. Current stops flowing through optically coupled photodiode 117, turning off transistor 118 within optoisolator 115. Current flowing through resistor 107 then flows through the base of transistor 114 turning it on. This discharges the gate capacitance of power MOSFET 113 through resistor 109, very rapidly turning off MOSFET 113; and opening switch 1.

Simultaneously, the low voltage on lead 180 turns off transistor 125 which has been receiving base current from resistor 122. Capacitor 124 is connected between the base and emitter of transistor 125 to simulate the time delay associated with optoisolator 115, so that transistor 125 turns off at substantially the same instant that transistor 118 turns off. The turn-off of transistor 125 allows current through resistor 126 to flow into the base of transistor 127, discharging the gate capacitance of MOSFET 131 and thus very rapidly turning it (switch 1A) off: opening switch 1A at the same time as the opening of switch 1.

Later in the pulse cycle when the output of pulse generator 138 on lead 350 becomes low, capacitor 147 discharges through resistor 145. This takes 1 to 1½ microseconds and after this time, the output lead 180 of NOR gate 148 goes high. (There is no such delay in the previous or following part of the pulse cycle when lead 180 goes low thereby turning off switches 1 and 1A.) However, there is a 1 to 1½ microsecond delay before lead 180 goes high thereby turning switch pairs 1 and 1A on.

Since all three of the switch pairs 1, 1A, 2, 2A and 3, 3A are controlled through a similar fast turn-off, slow turn-on circuits, the result is that on each transition, the previous switch turns off 1 to 1½ microseconds before the next switch turns on thereby avoiding short circuits.

Consider the turn-on of switches 1, 1A. When lead 180 goes high, transistor 119 turns on by means of base current supplied through resistor 120. This lights LED 116 in optoisolator 115 turning on photodiode 117 and amplifying transistor 118. Current through the collector of transistor 118 brings the base transistor 114 low and it turns off. The gate capacitance of MOSFET 113 charges up through 15 kilohm resistor 108 until it reaches a potential of about +10 volts, where zener diode 110 clamps it at that level. MOSFET 113 turns on as the gate swings up past about +5 volts. Meanwhile, the high level on lead 180 turns on transistor 125 with base current through resistor 122. Capacitor 124 delays this operation to match the time delay associated with optoisolator 115 so that both switches 1 and 1A will turn (an off) at the same time.

For switch 1, 5.6 volt, zener diode 104 and capacitor 105 set a regulated potential for operating the photodiode 117 in the optoisolator 115. Zener diode bias is supplied by 100 kilohm resistor 106. Overcurrent damage to transistor 113 (and transistor 131 which is effectively connected in series with it) is prevented by resistor 112 and transistor 111. If the current exceeds 0.8 ampere, the voltage drop across resistor 112 turns on transistor 111 shorting to the gate of MOSFET transistor 113 to a low potential tending to turn it off. This description also applies to switch pairs 2-2A and 3-3A as well as switch pair 1-1A.

All transistors in this figure, with the exception of the MOSFETs MTP1N60 and the transistors in the optoisolators, are Type 2N3904. Switch turn-off before the next switch turn-on is primarily provided by the resistor-diode-capacitor networks 145- 146-147, 175- 176- 177 and 170- 171- 172 respectively at the inputs of NOR gates 148, 178 and 173. They cause each of the respective switch pairs 1-1A, 2-2A and 3-3A to turn off about 1 to 1.5 microseconds before the next one starts to turn on.

The size of resistors 108 and 126 in switches 1 and 1A is sufficiently large so that the turn-on time of the MOSFET transistors 113 and 131 is about ½ microsecond. This also applies to the MOSFETs in switches 2, 2A, 3 and 3A. Shorter turn-on times than ½ microsecond provide some degree of problems with transient reverse recovery currents through the diodes connected to the electrophoresis tank 85. The MOSFET turn-off times, which are set by the resistors 109 and 129 in switches 1 and 1A (and corresponding resistors in switches 2, 2A, 3 and 3A), are about three times as fast as the turn-on times to provide further ensurance that one pair of MOSFET switches turns off before the next pair turns on.

The gates of switch 1 (and of course also switches 2 and 3) and associated driving circuitry operate from an isolated power supply. Each such isolated supply is derived from low voltage AC circuitry including a stepdown transformer 289 having its primary connected to 120 volt AC mains on its primary. Its secondary produces 15 volts AC on leads 270 and 271.

To supply the drive power for the switches 1,1A, 2,2A, and 3,3A, a first winding (the 15 volt winding) of a similar transformer 101 is connected to these two leads. Its second winding produces an AC voltage sufficient to develop +130 volts DC on lead 262 when half wave rectified by diode 103 connected to a first side of the second winding; the rectified DC is smoothed by filter capacitor 102. The negative end of the filter capacitor is connected at 272 to the second terminal of the second voltage winding of the transformer 101 and to the pulse output terminal 132. The pulse output terminal 132 is the common or reference potential for the circuitry of switch 1. The 15 volts AC on leads 271 and 270 supply the floating drive power for switches 2 and 3 in an identical manner.

To supply a positive 20 volts for the drive circuits or 15 volts for the logic circuits, the potential between leads 270 and 271 is also rectified by bridge rectifier diodes 291, 292, 293 and 294 to provide +20 volts. Conventional +15 volt integrated circuit regulator 296 is supplied with this +20 volts and produces the regulated +15 volts also required in the pulse generator and logic circuitry.

When control terminal 301 is low, the collector of transistor 166 is high, putting a logical high on the D input of D flip-flop 153. The next time the output on lead 350 from pulse generator 128 goes high, the Q output of 153 is clocked high providing an enabling input to NAND gate 154. This brings the output of pin 11 of NAND gate 154 low and the output of pin 10 of NOR gate 155 high. This enables the input 1 of NAND gate 174 and input 5 of NAND gate 169.

When the cycle timer (not shown) connected to terminal 302 is logically low, the collector of transistor 162 goes high putting a high on the D input of flip-flop 168; and if the cycle timer is high, the D input of flip-flop 168 is low. At the end (427 or 427A; FIG. 4) of every pulse cycle (422), pulse generator 138 produces a very short duration positive pulse at its pin 4. This turns on transistor 150 through resistor 149, bringing its collector low. This brings the output of pin 10 of NAND gate 152 high producing a clock signal at pin 3 of flip-flop 168.

If the cycle timer connected to terminal 302 has changed state since the preceding clock pulse, the Q output at pin 1 and the not Q output at pin 2 of flip-flop 168 reverse their logical states. Flip-flop 168 is used to ensure that the migration vector does not change in the middle of a high frequency pulse alternation cycle by synchronizing migration vector changes with the end of a high frequency pulse cycle. The network composed of diode 176, resistor 175, capacitor 177 and NOR gate 178 ensures that switch pair 2-2A turns on only after the previously on switch pair turns off. NOR gate 178 controls switch pair 2-2A through lead 181. NOR gate 173 controls switch pair 3-3A through lead 182.

While it may be possible to perform some of the processes of this invention using more general apparatuses such as the aforementioned PACE systems, simpler less expensive equipment can be used. For example, it is only necessary to have electrodes on four sides of the gel and simple controls for pulse frequencies and polarity changes rather than a computer which varies values for several electrodes and the complicating circuitry. The electrodes are open circuited by a diode transistor combination when not supplying pulses rather than being clamped to a fixed potential and thus sneak paths are avoided in relatively inexpensive circuit adapted to perform the method of this application.

As can be understood from the above description, the electrophoresis apparatus of this invention has several advantages, such as for example: (1) it is relatively uncomplex and inexpensive; (2) it is able to separate large DNA molecules; (3) it does not result in bent or curved lanes of travel of the DNA; (4) it is versatile in handling different sizes of DNA strands; and (5) its uncomplex nature makes it easy to use. The internal electronic design which provides for this versatility does not require an external computer or a matrix of matched or expensive circuits, each of which must be independently adjusted or programmed. Thus, it is easier to use and its cost is much lower than the PACE system.

Although a preferred embodiment of the invention is described with some particularity, many modifications and variations of the preferred embodiment are possible without deviating from the invention. Therefore, it is to be understood that within the scope of the appended claims the invention may be practiced other than as specifically described.

What is claimed is:

1. A method for separating large DNA by pulsed field gel electrophoresis comprising the steps of:

applying a first pulsed electric field parallel to the direction of overall DNA migration with first pulse durations;

applying a second pulsed electric field perpendicular to the direction of overall migration, wherein said second pulsed electric field starts with a first polarity and undergoes a first continuous time period of rapid pulses having pulse durations occuring between different ones of said first pulsed electric field at a frequency too high to induce frequency-synchronous gross conformational change in the DNA;

continuing said first continuous time period of rapid pulses for a time greater than one second, followed by a first reversal of the polarity of the said second pulsed electric field; wherein said reversed polarity second pulsed electric field undergoes a second continuous time period of rapid pulses interspersed with said first pulsed electric field at a frequency too high to induce frequency-synchronous gross conformation change in the DNA;

continuing said second continuous time period of rapid pulses for a time greater than one second, followed by second reversal of the second pulsed electric field back to the said first polarity wherein a pattern of alternate first and second pulses electric fields similar to that during said first continuous time period of rapid pulses is created; and repeating the sequence of alternating first and second electric field pulses for an extended period of time.

2. The method of claim 1 wherein the time durations of the said first polarity and said reversed polarity portions of each of the said first and second continuous time periods are equal; and the duty factor of said first polarity and reverse polarity second pulsed electric fields are equal.

3. The method of claim 2 wherein the said first and second pulsed electric fields have a frequency selected between 10 hertz and 1 megahertz and have pulses which alternate with each other.

4. The method of claim 3 further including the step of adjusting said frequency above and below a frequency on the order of 3 kilohertz to optimize DNA/gel interaction.

5. The method of claim 4 in which the steps of applying said first pulsed and second pulsed electric fields comprises the step of: controlling the time of said first and second pulsed electric fields with a repeated timing pulse the width of which can be varied from zero to substantially one period of the said frequency, wherein a first migration vector of DNA during the time the second pulsed electric field has said first polarity may be varied through an angle of 0 degrees to almost 90 degrees to one side of the overall direction of migration, and during the time the second pulsed electric field has the said second polarity, migration follows a second vector at an equal angle on the opposite side of the overall direction of migration, whereby the DNA will appear to follow a substantially straight line path in the direction of overall migration which is at an angle midway between the said first migration vector and said second migration vector.

6. The method of claim 5 in which the step of applying said first pulsed and second pulsed electric fields comprises the step of: generating more than 100 pulses of the said first pulsed electric field and the said second pulsed electric field during each of the said first and second continuous time periods.

7. The method of claim 6 in which the step of alterating said first pulsed and second pulsed electric fields comprises the step of: generating first and second pulsed electric fields that are substantially uniform in intensity and density across the gel.

8. The method of claim 1 wherein the said first and second pulsed electric fields have a frequency selected between 10 hertz and 1 megahertz and have pulses which alternate with each other.

9. The method of claim 8 further including the step of adjusting said frequency above and below a frequency on the order of 3 kilohertz to optimize DNA/gel interaction.

10. The method of claim 9 in which the steps of applying said first pulsed and second pulsed electric fields comprises the step of: controlling the time of said first and second pulsed electric fields with a repeated timing pulse the width of which can be varied from zero to substantially one period of the said frequency, wherein a first migration vector of DNA during the time the second pulsed electric field has said first polarity may be varied through an angle of 0 degrees to almost 90 degrees to one side of the overall direction of migration, and during the time the second pulsed electric field has the said second polarity, migration follows a second vector at an equal angle on the opposite side of the overall direction of migration, whereby the DNA will appear to follow a substantially straight line path in the direction of overall migration which is at an angle midway between the said first migration vector and said second migration vector.

11. The method of claim 10 in which the step of applying said first pulsed and second pulsed electric fields comprises the step of: generating more than 100 pulses of the said first pulsed electric field and the said second pulsed electric field during each of the said first and second continuous time periods.

12. The method of claim 11 in which the step of alterating said first pulsed and second pulsed electric fields comprises the step of: generating first and second pulsed electric fields that are substantially uniform in intensity and density across the gel.

13. The method of claim 1 further including the step of adjusting said frequency above and below a frequency on the order of 3 kilohertz to optimize DNA/gel interaction.

14. The method of claim 13 in which the steps of applying said first pulsed and second pulsed electric fields comprises the step of: controlling the time of said first and second pulsed electric fields with a repeated timing pulse the width of which can be varied from zero to substantially one period of the said frequency, wherein a first migration vector of DNA during the time the second pulsed electric field has said first polarity may be varied through an angle of 0 degrees to almost 90 degrees to one side of the overall direction of migration, and during the time the second pulsed electric field has the said second polarity, migration follows a second vector at an equal angle on the opposite side of the overall direction of migration, whereby the DNA will appear to follow a substantially straight line path in the direction of overall migration which is at an angle midway between the said first migration vector and said second migration vector.

15. The method of claim 14 in which the step of applying said first pulsed and second pulsed electric fields comprises the step of: generating more than 100 pulses of the said first pulsed electric field and the said second pulsed electric field during each of the said first and second continuous time periods.

16. The method of claim 15 in which the step of alterating said first pulsed and second pulsed electric fields comprises the step of: generating first and second pulsed electric fields that are substantially uniform in intensity and density across the gel.

17. The method of claim 1 in which the steps of applying said first pulsed and second pulsed electric fields comprises the step of: controlling the time of said first and second pulsed electric fields with a repeated timing pulse the width of which can be varied from zero to substantially one period of the said frequency, wherein a first migration vector of DNA during the time the second pulsed electric field has said first polarity may be varied through an angle of 0 degrees to almost 90 degrees to one side of the overall direction of migration, and during the time the second pulsed electric field has the said second polarity, migration follows a second vector at an equal angle on the opposite side of the overall direction of migration, whereby the DNA will appear to follow a substantially straight line path in the direction of overall migration which is at an angle midway between the said first migration vector and said second migration vector.

18. The method of claim 17 in which the step of applying said first pulsed and second pulsed electric fields comprises the step of: generating more than 100 pulses of the said first pulsed electric field and the said second pulsed electric field during each of the said first and second continuous time periods.

19. The method of claim 18 in which the step of alterating said first pulsed and second pulsed electric fields comprises the step of: generating first and second pulsed electric fields that are substantially uniform in intensity and density across the gel.

20. The method of claim 1 in which the step of applying said first pulsed and second pulsed electric fields comprises the step of: generating more than 100 pulses of the said first pulsed electric field and the said second pulsed electric field during each of the said first and second continuous time periods.

21. The method of claim 20 in which the step of alterating said first pulsed and second pulsed electric fields comprises the step of: generating first and second pulsed electric fields that are substantially uniform in intensity and density across the gel.

22. The method of claim 1 in which the step of alterating said first pulsed and second pulsed electric fields comprises the step of: generating first and second pulsed electric fields that are substantially uniform in intensity and density across the gel.

* * * * *